United States Patent [19]

Reiffenrath et al.

[11] Patent Number: 5,204,477
[45] Date of Patent: Apr. 20, 1993

[54] PYRIDINE DERIVATIVES IN LIQUID CRYSTALLINE MEDIUM USEFUL FOR ELECTROOPTICAL DISPLAY ELEMENTS

[75] Inventors: Volker Reiffenrath, Rossdorf; Eike Poetsch, Mühltal; Volker Meyer, Gross-Zimmern; Herbert Plach, Darmstadt, all of Fed. Rep. of Germany

[73] Assignee: Merck Patent Gesellschaft mit beschrankter Haftung, Fed. Rep. of Germany

[21] Appl. No.: 623,394

[22] PCT Filed: Sep. 12, 1990

[86] PCT No.: PCT/EP90/01535
§ 371 Date: Nov. 29, 1990
§ 102(e) Date: Nov. 29, 1990

[87] PCT Pub. No.: WO91/04249
PCT Pub. Date: Apr. 4, 1991

[30] Foreign Application Priority Data

Sep. 22, 1989 [GB] United Kingdom ............... 8921519

[51] Int. Cl.$^5$ ............... C07D 213/62; C07D 213/63; C07D 213/64
[52] U.S. Cl. ............... 546/303; 546/290; 546/302; 340/810
[58] Field of Search ............... 546/303, 302, 290

[56] References Cited

FOREIGN PATENT DOCUMENTS 3736489 5/1989 Fed. Rep. of Germany ...... 560/103

OTHER PUBLICATIONS

Chemical Abstracts, vol. 109, No. 2, p. 596, Abst. No. 15315-z, Jul. 11, 1988.
Chemical Abstracts, vol. 102, No. 19, p. 603, Abst. No. 166,578-u, May 13, 1985.

*Primary Examiner*—Alan L. Rotman
*Attorney, Agent, or Firm*—Millen, White, Zelano & Branigan

[57] ABSTRACT

The invention relates to pyridine derivatives of the formula I

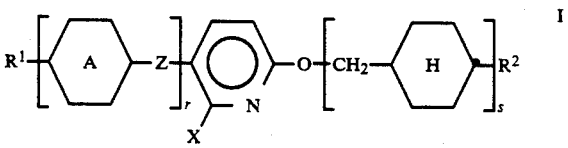

wherein $R^1$, A, Z, r, X, s and $R^2$ have the meaning given in claim 1, and their use as components for liquid crystal media for electrooptical display elements based on the ECB effect.

2 Claims, No Drawings

PYRIDINE DERIVATIVES IN LIQUID CRYSTALLINE MEDIUM USEFUL FOR ELECTROOPTICAL DISPLAY ELEMENTS

The invention relates to pyridine derivatives of the formula I

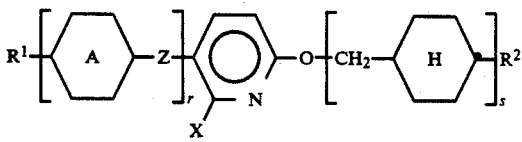

wherein
- $R^1$ is a straight-chain alkyl, alkoxy, alkenyl or oxaalkyl group with up to 15 C atoms in the alkyl residue, in case of $X=F$, the $R^1$ groups may also be branched,
- A is 1,4-cyclohexylene or 1,4-phenylene which is unsubstituted or mono- or polysubstituted by F, and wherein one or two CH groups may also be replaced by N,
- Z is $-CH_2-CH_2-$, $-C\equiv C-$ or a single bond,
- r is 0, 1 or 2,
- s is 0 or 1,
- r+s is 1, 2 or 3,
- $R^2$ is alkyl, alkenyl, oxaalkyl or alkylcarbonyl with up to 15 C atoms in the alkyl residue
and
- X is H or F,
with the proviso that
X is a fluoro atom if
$R^1$ and $R^2$ are straight-chain alkyl groups, r is 1, s is 0, A is an unsubstituted 1,4-phenylene and Z is a single bond.

The invention also relates to liquid crystal media, especially for electrooptical display elements based on the ECB effect, which contain at least one compound of the pyridine derivatives of the formula I.

For the sake of simplicity in the following, Phe is an unsubstituted 1,4-phenylene group, PheF is a mono- or disubstituted 1,4-phenylene group, Cyc is a trans-1,4-cyclohexylene group, Pyd is a pyridine-2,5-diyl group and Pyr is a pyrimidine-2,5-diyl group.

The compounds of the formula I can be used as components of liquid crystalline media, in particular for displays which are based on the principle of the twisted cell, the guest-host effect, the effect of the deformation of aligned phases or the effect of dynamic scattering.

Compounds of the formula I are preferably also suitable for the use as components in liquid crystalline media for displays which are based on the ECB effect. Furthermore, some of the compounds of the formula I are also suitable for the use as components of STN mixtures.

Similar pyridine compounds are disclosed, e.g. in WO 87/4158 or in DE 38 14 346. However, none of these disclosed pyridines show an oxygen atom near the N atom of the pyridine ring and they do not have the excellent properties of the compounds of the present invention.

The ECB (electrically controlled birefringence) effect or DAP (deformation of aligned phases) effect was described for the first time in 1971 (M. F. Schieckel and K. Fahrenschon, "Deformation of nematic liquid crystals with vertical orientation in electrical fields", Appl. Phys. Lett. 19 (1971), 3912). Works by J. F. Kahn (Appl. Phys. Lett. 20 (1972), 1193) and G. Labrunie and J. Robert (J. Appl. Phys. 44 (1973), 4869) followed.

The works by J. Robert and F. Clerc (SID 80 Digest Techn. Papers (1980), 30), J. Duchene (Displays 7 (1986), 3) and H. Schad (SID 82 Digest Techn. Papers (1982), 244) have shown that liquid crystal media must have high values for the ratio of the elastic constants $K_3/K_1$, high values for the optical anisotropy $\Delta n$ and negative values for the dielectrical anisotropy $\Delta\epsilon$ in order to be able to be used for highly informative display elements based on the ECB effect.

Electrooptical display elements based on the ECB effect have a homoeotropic edge orientation, that is to say the liquid crystal medium has negative dielectric anisotropy.

For technical use of this effect in electrooptical display elements, LC media which must meet numerous requirements are required. The chemical stability towards moisture, air and physical influences, such as heat, infrared, visible and ultraviolet radiation and constant and alternating electrical fields, are particularly important here. A liquid crystal mesophase in a suitable temperature range and a low viscosity are furthermore required of technically useful LC media.

In none of the series of compounds with a liquid crystal mesophase which are known to date is there a single compound which meets all these requirements. Mixtures of two to 25, preferably three to 18, compounds are therefore as a rule prepared in order to obtain substances which can be used as LC media. However, it has not been possible for optimum media to be easily prepared in this manner, since no liquid crystal materials with significantly negative dielectric anisotropy and/or correspondingly high optical anisotropy and/or particularly high values for $K_3/K_1$ and adquate long-term stability have as yet been available.

There is thus still a great need for liquid crystal media with favorable meso ranges, high values of $K_3/K_1$, high optical anisotropy $\Delta n$, negative dielectric anisotropy $\Delta\epsilon$ and high long-term stability.

Suprisingly, it has been found that the addition of compounds of the formula I produces liquid crystal media which fulfil all the above mentioned criteria very well indeed.

In addition, by providing the compounds of the formula I, the whole palette of liquid crystalline substances which are suitable from a variety of technical viewpoints for the preparation of nematic mixtures, has been considerably broadened.

The compounds of the formula I have a wide area of application. Depending on the choice of substituents, these compounds can serve as base materials from which the major part of liquid crystalline media are made up; liquid crystalline base materials from other classes of compounds can, however, also be added to compounds of the formula I, for example to optimize the dielectric and/or optical anisotropy of a dielectric of this type. The compounds of the formula I are also suitable as intermediates for the preparation of other substances which can be used as constituents of liquid crystalline media.

The compounds of the formula I are colourless in their pure form and form liquid crystalline mesophases in a temperature range which is favorable for electrooptical use. They are very chemically and thermally stable and are very stable to light.

The invention accordingly relates to the compounds of the formula I and the use of these compounds as components of liquid crystalline media and as components of liquid crystalline media for electrooptical display elements based on the ECB effect. The invention furthermore relates to liquid crystalline media, especially for electrooptical display elements based on the ECB effect which contain at least one compound of the formula I, and also to electrooptical display elements, which contain media of this type.

In the foregoing and in what follows $R^1$, - A -, Z, r, X, s and $R^2$ have the meaning indicated, unless something else is specifically stated.

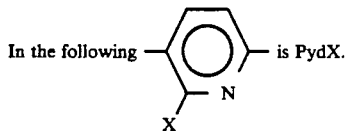

The compounds of the formula I accordingly also include compounds of the partial formulae I1 to I3 (having two rings), I4 to I9 (having three rings) and I10 to I13 (having four rings);

| | |
|---|---|
| $R^1$-PydX-OCH$_2$-Cyc-R$^2$ | I1 |
| $R^1$-A-PydX-OR$^2$ | I2 |
| $R^1$-A-Z-PydX-OR$^2$ | I3 |
| $R^1$-A-PydX-OCH$_2$-Cyc-R$^2$ | I4 |
| $R^1$-A-Z-PydX-OCH$_2$-Cyc-R$^2$ | I5 |
| $R^1$-A-A-PydX-OR$^2$ | I6 |
| $R^1$-A-Z-A-PydX-OR$^2$ | I7 |
| $R^1$-A-Z-A-Z-PydX-OR$^2$ | I8 |
| $R^1$-A-A-Z-PydX-OR$^2$ | I9 |
| $R^1$-A-A-PydX-OCH$_2$-Cyc-R$^2$ | I10 |
| $R^1$-A-Z-A-PydX-OCH$_2$-Cyc-R$^2$ | I11 |
| $R^1$-A-A-Z-PydX-OCH$_2$-Cyc-R$^2$ | I12 |
| $R^1$-A-Z-A-Z-PydX-OCH$_2$-Cyc-R$^2$ | I13 |

The preferred compounds of the partial formula I1 include those of the partial formulae I1a to I1d:

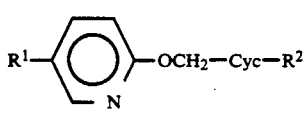
I1a

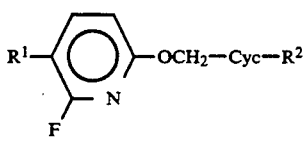
I1b

| | |
|---|---|
| Alkyl-PydX-OCH$_2$-Cyc-Alkyl | I1c |
| Alkoxy-PydX-OCH$_2$-Cyc-Alkyl | I1d |

Among these, those of the formulae I1a and I1c are particularly preferred.

The preferred compounds of the partial formula I2 include those of the partial formulae I2a to I2l:

| | |
|---|---|
| $R^1$-Phe-PydX-OR$^2$ | I2a |
| $R^1$-PheF-PydX-OR$^2$ | I2b |
| $R^1$-Cyc-PydX-OR$^2$ | I2c |
| $R^1$-Pyd-PydX-OR$^2$ | I2d |
| $R^1$-Pyr-PydX-OR$^2$ | I2e |

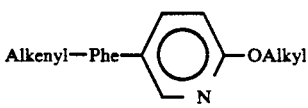
I2f

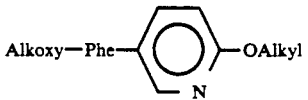
I2g

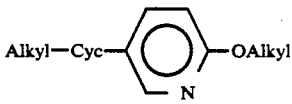
I2h

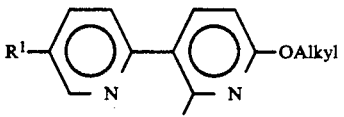
I2i

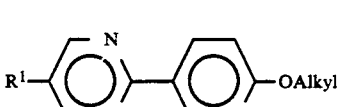
I2j

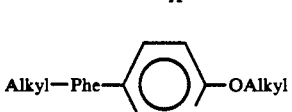
I2k

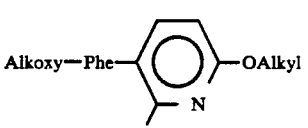
I2l

Among these, those of the formulae I2a, I2c, I2g, I2k and I2l are particularly preferred. The preferred compounds of the partial formula I3 include those of the partial formulae I3a to I3v:

| | |
|---|---|
| $R^1$-Phe-C≡C-PydX-OR$^2$ | I3a |
| $R^1$-PheF-C≡C-PydX-OR$^2$ | I3b |
| $R^1$-Phe-Ch$_2$CH$_2$-PydX-OR$^2$ | I3c |
| $R^1$-Cyc-C≡C-PydX-OR$^2$ | I3d |

R¹-Cyc-CH₂CH₂-PydX-OR²  I3e

R¹-PheF-Ch₂Ch₂-PydX-OR²  I3f

R¹-Pyd-Ch₂Ch₂-PydX-OR²  I3g

R¹-Pyr-Ch₂Ch₂-PydX-OR²  I3h

R¹-Pyd-C≡C-PydX-OR²  I3i

R¹-Pyr-C≡C-PydX-OR²  I3j

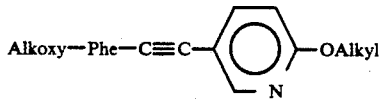  I3k

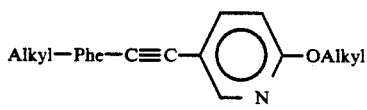  I3l

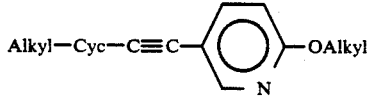  I3m

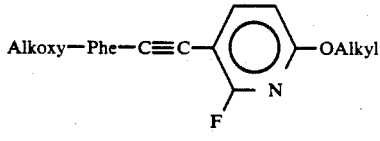  I3n

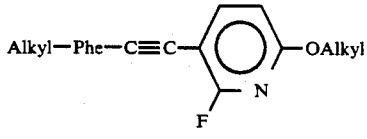  I3o

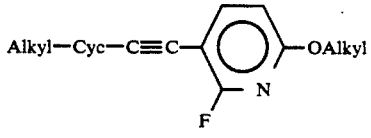  I3p

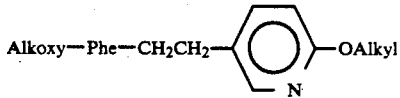  I3q

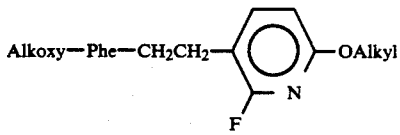  I3r

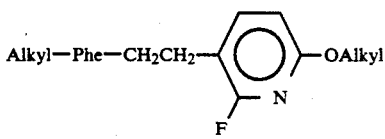  I3s

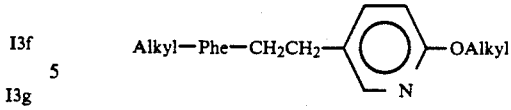  I3t

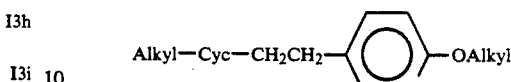  I3u

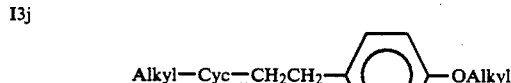  I3v

Among these, those of the formulae I3a, I3b, I3c, I3d, I3e, I3k, I3l, I3m, I3n, I3o, I3q, I3s and I3t are particularly preferred.

The preferred compounds of the partial formula I4 include those of the partial formulae I4a to I4k:

R¹-Phe-PydX-OCH₂-Cyc-R²  I4a

R¹-PheF-PydX-OCH₂Cyc-R²  I4b

R¹-Cyc-PydX-OCH₂-Cyc-R²  I4c

Alkyl-Cyc-PydX-OCH₂-Cyc-Alkyl  I4d

Alkyl-Phe-PydX-OCH₂-Cyc-Alkyl  I4e

Alkyl-PheF-PydX-OCH₂-Cyc-Alkyl  I4f

Alkoxy-Phe-PydX-OCH₂-Cyc-Alkyl  I4g

Alkoxy-PheF-PydX-OCH₂-Cyc-Alkyl  I4h

R¹-Pyd-PydX-OCH₂-Cyc-Alkyl , I4i

R¹-Pyr-PydX-OCH₂-Cyc-Alkyl  I4j

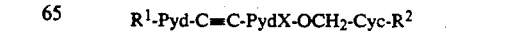  I4k

Among these, those of the formulae I4a, I4b, I4d, I4g and I4k are particularly preferred.

The preferred compounds of the partial formula I5 include those of the partial formulae I5a to I5j:

R¹-Phe-CH₂Ch₂-PydX-OCH₂-Cyc-R²  I5a

R¹-Phe-C≡C-PydX-OCH₂-Cyc-R²  I5b

R¹-PheF-C≡C-PydX-OCH₂-Cyc-R²  I5c

R¹-PheF-CH₂CH₂-PydX-OCH₂-Cyc-R²  I5d

R¹-Cyc-ChCh₂-PydX-OCH₂-Cyc-R²  I5e

R¹-Cyc-C≡C-PydX-OCH₂-Cyc-R²  I5f

R¹-Pyd-C≡C-PydX-OCH₂-Cyc-R²  I5g

R¹-Pyr-C≡C-PydX-OCH₂-Cyc-R²  I5h

R¹-Pyr-CH₂CH₂-PydX-OCH₂-Cyc-R²  15i

R¹-Pyd-CH₂CH₂-PydX-OCH₂-Cyc-R²  15j

The preferred compounds of the partial formula I6 include those of the partial formulae I6a to I6x:

R¹-Phe-Phe-PydX-OR²  I6a

R¹-Cyc-Cyc-PydX-OR²  I6b

R¹-Cyc-Phe-PydX-OR²  I6c

R¹-Phe-Cyc-PydX-OR²  I6d

R¹-Pyd-Phe-PydX-OR²  I6e

R¹-Pyr-Phe-PydX-OR²  I6f

R¹-Pyd-Cyc-PydX-OR²  I6g

R¹-Pyr-Cyc-PydX-OR²  I6h

R¹-Phe-Pyr-PydX-OR²  I6i

R¹-Phe-Pyd-PydX-OR²  I6j

R¹-Cyc-Pyd-PydX-OR²  I6k

R¹-Cyc-Pyr-PydX-OR²  I6l

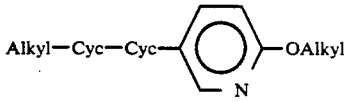  I6m

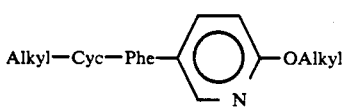  I6n

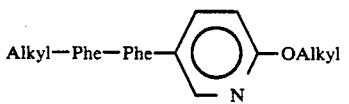  I6o

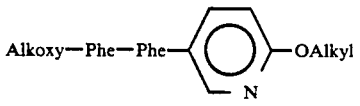  I6p

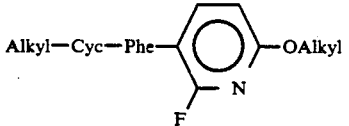  I6q

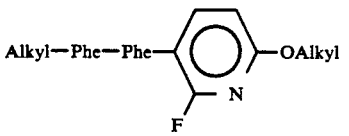  I6r

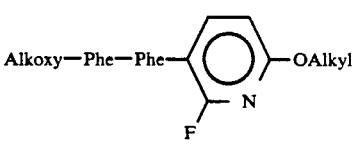  I6s

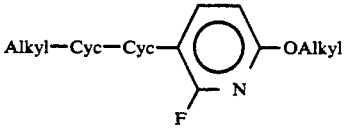  I6t

R¹-PheF-Phe-PydX-OR²  I6u

R¹-PheF-PheF-PydX-OR²  I6v

R¹-Phe-PheF-PydX-OR²  I6w

R¹-Cyc-PheF-PydX-OR²  I6x

Among these, those of the formulae I6a, I6b, I6c, I6m, I6n, I6o, I6p, I6q, I6r, I6s, I6w, I6x and I6t are particularly preferred.

The preferred compounds of the partial formulae I7 include those of the partial formulae I7a to I7z:

R¹-Phe-Ch₂Ch₂-Phe-PydX-OR²  I7a

R¹-Cyc-Ch₂Ch₂-Phe-PydX-OR²  I7b

R¹-Pyd-Ch₂Ch₂-Phe-PydX-OR²  I7c

R¹-Pyr-Ch₂Ch₂-Phe-PydX-OR²  I7d

R¹-Phe-Ch₂Ch₂-Cyc-PydX-OR²  I7e

R¹-Cyc-Ch₂Ch₂-Cyc-PydX-OR²  I7f

R¹-Phe-C≡C-Phe-PydX-OR²  I7g

R¹-Cyc-C≡C-Phe-PydX-OR²  I7h

R¹-Pyd-C≡C-Phe-PydX-OR²  I7i

R¹-Pyr-C≡C-Phe-PydX-OR²  I7j

R¹-Phe-C≡C-Cyc-PydX-OR²  I7k

R¹-Cyc-C≡C-Cyc-PydX-OR²  I7l

R¹-Phe-C≡C-Cyc-PydX-OR²  I7m

R¹-Phe-C≡C-Pyr-PydX-OR²  I7n

R¹-Phe-CH₂CH₂-Pyr-PydX-OR²  I7o

R¹-Phe-CH₂CH₂-Pyd-PydX-OR²  I7p

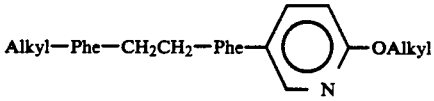  I7q

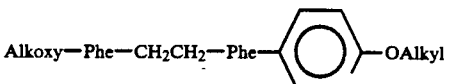  I7r

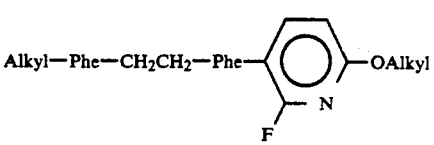  I7s

-continued

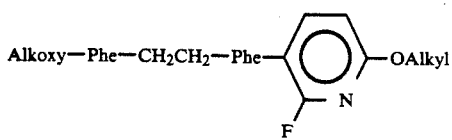  I7t

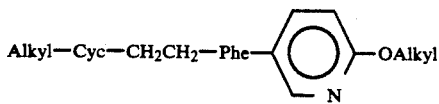  I7u

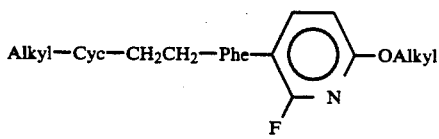  I7v

R$^1$-PheF-Z-Phe-PydX-OR$^2$  I7w

R$^1$-PheF-Z-PheF-PydX-OR$^2$  I7x

R$^1$-Phe-Z-PheF-PydX-OR$^2$  I7y

R$^1$-Cyc-X-PheF-PydX-OR$^2$  I7z

Among these, those of the formulae I7a, I7b, I7e, I7f, I7g, I7h, I7k, I7q, I7r, I7s, I7t, I7u, I7w, I7y, I7v and I7z are particularly preferred.

The preferred compounds of the partial formulae I8 include those of the partial formulae I8a to I8p:

R$^1$-Phe-CH$_2$CH$_2$-Phe-Z-PydX-OR$^2$  I8a

R$^1$-Phe-C≡C-Phe-Z-PydX-OR$^2$  I8b

R$^1$-Phe-Z-Cyc-Z-PydX-OR$^2$  I8c

R$^1$-Cyc-Z-Cyc-CH$_2$CH$_2$-PydX-OR$^2$  I8d

R$^1$-Cyc-C≡C-Phe-Z-PydX-OR$^2$  I8e

R$^1$-Pyd-Z-Phe-Z-PydX-OR$^2$  I8f

R$^1$-Pyr-Z-Phe-Z-PydX-OR$^2$  I8g

R$^1$-Cyc-Z-Pyd-Z-PydX-OR$^2$  I8h

R$^1$-Phe-Z-Pyr-Z-PydX-OR$^2$  I8i

R$^1$-Phe-Z-Pyd-Z-PydX-OR$^2$  I8j

R$^1$-Cyc-CH$_2$CH$_2$-Pyr-Z-PydX-OR$^2$  I8k

R$^1$-PheF-Z-Phe-Z-PydX-OR$^2$  I8l

R$^1$-PheF-Z-PheF-Z-PydX-OR$^2$  I8m

R$^1$-Phe-Z-PheF-Z-PydX-OR$^2$  I8n

R$^1$-PheF-Z-Cyc-Z-PydX-OR$^2$  I8o

R$^1$-Cyc-Z-PheF-Z-PydX-OR2  I8p

The preferred compounds of the partial formula I9 include those of the partial formulae I9a to I9ab:

R$^1$-Phe-Phe-CH$_2$CH$_2$-PydX-OR$^2$  I9a

R$^1$-Phe-Phe-C≡C-PydX-OR$^2$  I9b

R$^1$-Phe-Cyc-C≡C-PydX-OR$^2$  I9c

R$^1$-Phe-Cyc-CH$_2$CH$_2$-PydX-OR$^2$  I9d

R$^1$-Pyd-Phe-C≡C-PydX-OR$^2$  I9e

R$^1$-Pyr-Phe-CH$_2$CH$_2$-PydX-OR$^2$  I9f

R$^1$-Cyc-Phe-CH$_2$CH$_2$-PydX-OR$^2$  I9g

R$^1$-Cyc-Phe-C≡C-PydX-OR$^2$  I9h

R$^1$-Cyc-Cyc-C≡C-PydX-OR$^2$  I9i

R$^1$-Cyc-Cyc-CH$_2$CH$_2$-PydX-OR$^2$  I9j

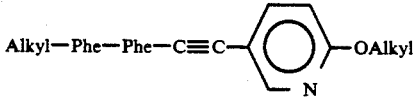  I9k

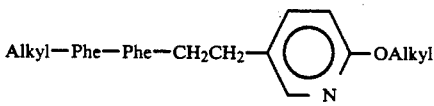  I9l

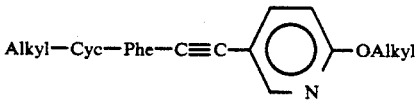  I9m

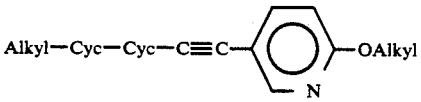  I9n

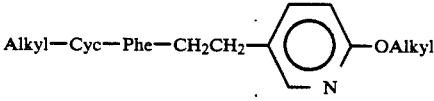  I9o

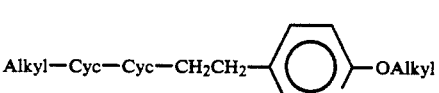  I9p

Alkyl—Phe—Phe—C≡C—PydX—OAlkyl  I9q

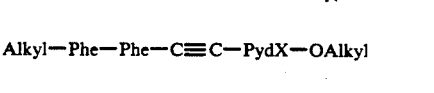  I9r

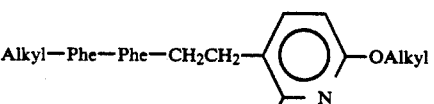  I9s

  I9t

-continued

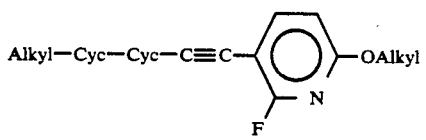 19u

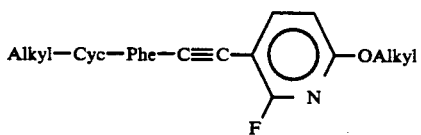 19v

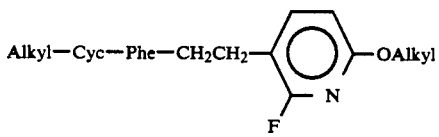 19w

| | |
|---|---|
| R$^1$-PheF-Phe-Z-PydX-OR$^2$ | 19x |
| R$^1$-PheF-PheF-Z-PydX-OR$^2$ | 19y |
| R$^1$-Phe-PheF-Z-PydX-OR$^2$ | 19z |
| R$^1$-Cyc-PheF-Z-PydX-OR$^2$ | 19aa |
| R$^1$-PheF-Cyc-Z-PydX-OR$^2$ | 19ab |

The preferred compounds of the partial formulae I10 to I13 include those of the partial formulae I10a to I10r:

| | |
|---|---|
| R$^1$-Phe-Phe-PydX-OCH$_2$-Cyc-R$^2$ | I10a |
| R$^1$-Cyc-Phe-PydX-OCH$_2$-Cyc-R$^2$ | I10b |
| R$^1$-Cyc-Cyc-PydX-OCH$_2$-Cyc-R$^2$ | I10c |
| R$^1$-Phe-CH$_2$CH$_2$-Phe-PydX-OCH$_2$-Cyc-R$^2$ | I10d |
| R$^1$-Phe-C≡C-Phe-PydX-OCH$_2$-Cyc-R$^2$ | I10e |
| R$^1$-Cyc-Z-Phe-PydX-OCH$_2$-Cyc-R$^2$ | I10f |
| R$^1$-Cyc-Cyc-CH$_2$CH$_2$-PydX-OCH$_2$Cyc-R$^2$ | I10g |
| R$^1$-Phe-Phe-Z-PydX-OCH$_2$-Cyc-R$^2$ | I10h |
| R$^1$-Cyc-Phe-Z-PydX-OCH$_2$-Cyc-R$^2$ | I10i |
| R$^1$-Cyc-Z-Phe-PydX-OCH$_2$-Cyc-R$^2$ | I10j |
| R$^1$-Phe-Z-Phe-CH$_2$CH$_2$-PydX-OCH$_2$-Cyc-R$^2$ | I10k |
| R$^1$-PheF-Phe-PydX-OCH$_2$-Cyc-R$^2$ | I10l |
| R$^1$-PheF-PheF-PydX-OCH$_2$-Cyc-R$^2$ | I10m |
| R$^1$-Phe-PheF-PydX-OCH$_2$-Cyc-R$^2$ | I10n |
| R$^1$-Cyc-PheF-PydX-OCH$_2$-Cyc-R$^2$ | I10o |
| R$^1$-Cyc-PheF-Z-PydX-OCH$_2$-Cyc-R$^2$ | I10p |
| R$^1$-Cyc-Z-PheF-OCH$_2$-Cyc-R$^2$ | I10q |
| R$^1$-PheF-Phe-Z-PydX-OCH$_2$-Cyc-R$^2$ | I10r |

In the compounds of the formulae above and below R$^1$ is preferably a straight-chain alkyl, alkoxy or oxaalkyl group. If X is a fluor atom, then R$^1$ is preferably also a branched alkyl, alkoxy or oxaalkyl group.

R$^2$ is preferably an alkyl, oxaalkyl or alkylcarbonyloxy group, which also may be branched.

Furthermore, compounds of the formula I are preferred in which R$^1$ and/or R$^2$ are alkenyl groups.

However, straight-chain alkyl groups are particularly preferred.

A is preferably 1,4-cyclohexylene or 1,4-phenylene, which can be substituted by fluorine (PheF). PheF in the compounds of the formulae above and below has the following preferred meanings:

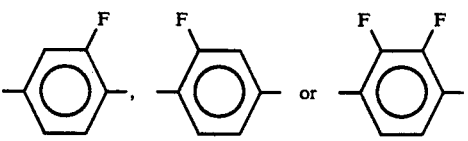

Furthermore, compounds of formula I are preferred in which A denotes 1,4-phenylene wherein one or two CH groups are replaced by N atoms. Accordingly pyridine-2,5-diyl and pyrimidine-2,5-diyl groups are particularly preferred.

Z is preferably a single bond or a —CH$_2$CH$_2$— group. Also preferred is —C≡C—.

r is preferably 1 or 2, s is 0 or 1, preferably 0, and r+s is preferably 1 or 2.

X is H or F, preferably H. When r is 2 the two rings A may be identical or different from one another.

Ir R$^1$ and/or R$^2$ are alkyl radicals in which one ("alkoxy" L or "oxaalkyl") CH2 group can also be replaced by an O atom, they can be straight-chain or branched. They are preferably straight-chain having 1, 2, 3, 4, 5, 6, 7, 8 or 9 C atoms and are accordingly preferably methyl, ethyl, propyl, butyl, pentyl, hexyl, heptyl, octyl, nonyl, ethoxy, propoxy, butoxy, pentoxy, hexoxy, heptoxy, octoxy, nonoxy, 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, furthermore decyl, undecyl, dodecyl, tridecyl, tetradecyl, pentadecyl, methoxy, decoxy, undecoxy, dodecoxy, tridecoxy, tetradecoxy, pentadecoxy, 2-, 3-, 4-, 5-, 6- or 7-oxaoctyl, 2-, 3-, 4-, 5-, 6-, 7- or 7-oxanonyl or 2-, 3-, 4-, 5-, 6-, 7-, 8- or 9-oxadecyl.

Compounds of the formula I having branched wing groups R$^1$ or R$^2$ can occasionally be of significance because of their better solubility in the customary liquid crystalline base materials, but in particular as chiral dopes, if they are optically active.

Branched groups of this type do not, as a rule, contain more than one chain branch. Preferred branched radicals are isopropyl, 2-butyl (=1-methylpropyl), isobutyl (=2-methylpropyl), 2-methylbutyl, isopentyl- (=3-methylbutyl), 2-methylpentyl, 3-methylpentyl, 2-ethylhexyl, 2-propylpentyl, 2-octyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy (=2-octyloxy), 2-oxa-3-methylbutyl, 3-oxa-4-methylpentyl, 4-methylhexyl, 2-nonyl, 2-decyl, 2-dodecyl, 6-methyloctoxy, 6-methyloctanoyl, 5-methylheptylcarbonyl, 2-methylbutyryl, 3-methylvaleryl, 4-methylhexanoyl, 2-methyl-3-oxapentyl or 2-methyl-3-oxahexyl.

For compounds having branched wing groups, formula I encompasses both the optical antipodes and racemates and also mixtures thereof.

Compounds of the partial formulae I2a, I2k, I2l, I6a, I6r and I6s having branched or/and optical active radicals are particularly preferred.

If $R^1$ and/or $R^2$ are an alkenyl radical the trans form is preferred. This alkenyl radical may be straight-chain or branched. It is preferably straight-chain and has 2 to 9 C atoms. Accordingly, it is particularly vinyl, prop-1-or prop-2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl.

Preferred compounds of the formula I and their subformulae are those in which at least one of the radicals contained therein has one of the indicated preferred meanings.

The compounds of the formula I are prepared by methods known per se, as are described in the literature (for example, in the standard reference works such as Houben-Weyl, Methoden der Organischen Chemie, Georg-Thieme-Verlag, Stuttgart), and, indeed, under reaction conditions which are known and suitable for the reactions mentioned. Variants may also be used which are known per se but are not mentioned in more detail here.

If desired, the starting substances can also be formed in situ, in such a manner that they are not isolated from the reaction mixture, but are immediately reacted further to the compounds of the formula I.

Preferred routes for the synthesis of compounds of the formula Ia are shown in the following reaction schemes.

A preferred route for the preparation of compounds of the formulae I2, I4, I6, I7, I10 and I11, wherein the ring A adjacent to the pyridine is an aromatic ring, is shown in scheme 1.

In the following schemes $R^3$ means $R^2$ or —CH$_2$—Cyc—$R^2$. LDA means lithium-diisopropylamide.

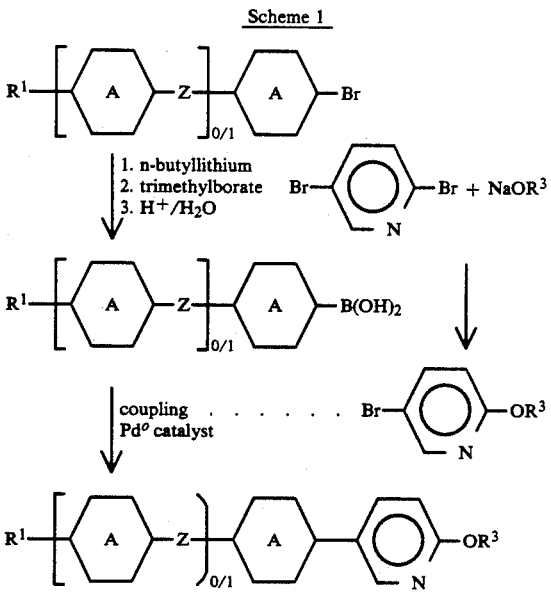

A preferred route for the synthesis of compounds of the formulae I3, I5, I8, I9, I12 and I13 is shown in scheme 2.

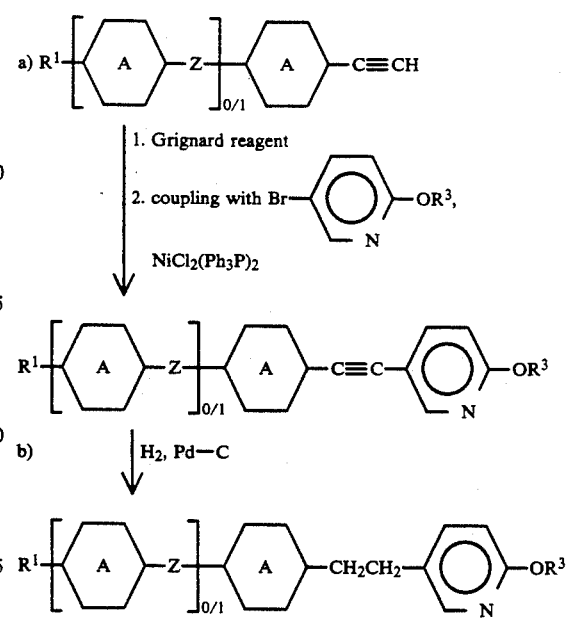

A preferred route for the synthesis of compounds of the formulae I2, I4, I6, I7, I10 and I 11 wherein the ring A adjacent to the pyridine is 1,4-cyclohexylene, is shown in scheme 3.

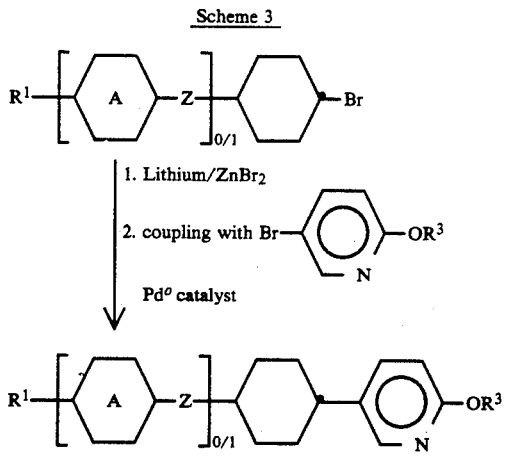

A preferred route to synthesize the pyridine products according to scheme 1 but having a fluorine substituent at the pyridine ring (X=F) is shown in scheme 4.

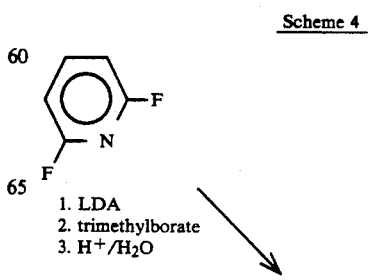

-continued
Scheme 4
A preferred route for the synthesis of compounds of the formulae I3, I5, I8, I9, I12 and I13 having a fluorine substituent of the pyridine ring (X=F) is given in Shceme 5.
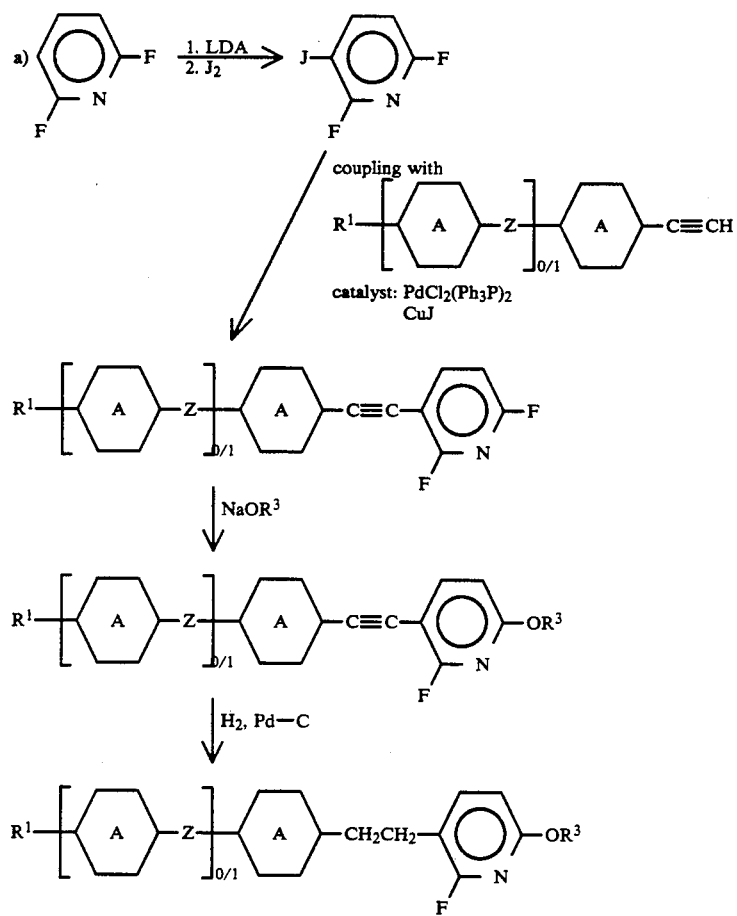
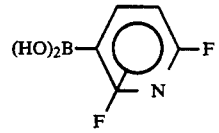
coupling with
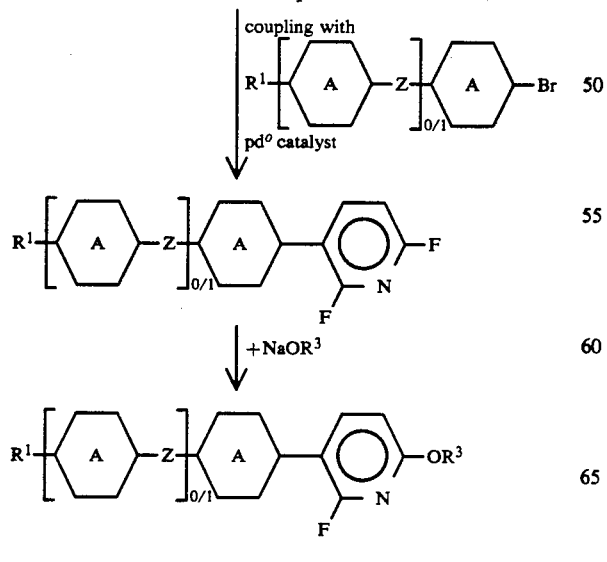
A preferred route for the synthesis of products according to scheme 3 but having a fluorine substituent at the pyridine ring is shown is scheme 6.
Scheme 6
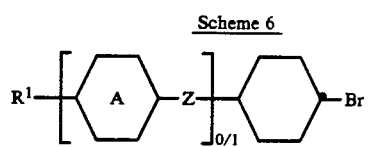
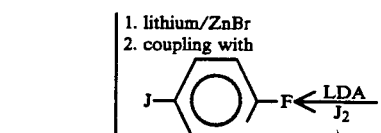
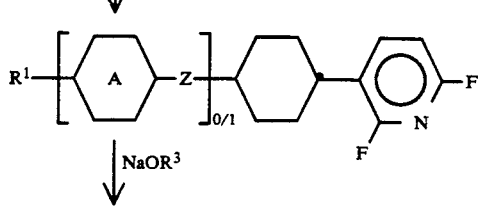

-continued
Scheme 6

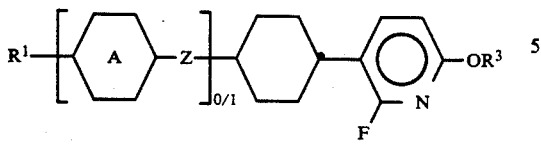 5

The compounds of the formula II can be prepared, for example, by coupling

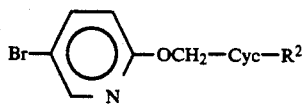 15 with $R^1Br$ in the presence of lithium/ZnBr and a catalyst, or by coupling

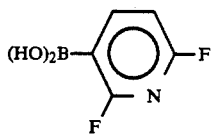 25 with $R^1Br$ in the presence of a Pd° catalyst and subsequent reaction with $NaOCH_2$-Cyc-$R^2$.

All starting materials are known or can be prepared in analogy to known compounds. Other routes are apparent to the skilled worker. All these steps and the corresponding reaction conditions are known to the skilled worker.

The liquid crystal media according to the invention for electrooptical display elements based on the ECB effect contain at least one compound of the formula I, these substances have a significantly negative dielectric anisotropy.

In addition to one or more compounds of the formula I (A) the liquid crystal media preferably contain components (B) having a pronounced nematogenicity and a low viscosity, and if appropriate further components (C) with a high clear point or components (D) with not more than a weakly positive dielectric anisotropy of at least 0.2. These additional components are preferably chosen from the following group of formulae II to VI

 II wherein $R^1$ and $R^2$ in each case independently of one another are an alkyl group with in each case 1 to 15 C atoms, wherein one or more CH2 groups can also be replaced by a grouping chosen from the group comprising —O—, —S—, —CO—, —CH—halogen—, —CHCN—, —O—CO—, —O—COO—, —CO—O— and —CH=CH— or also by a combination of two suitable groupings, two hetero atoms not being linked directly to one another, A is

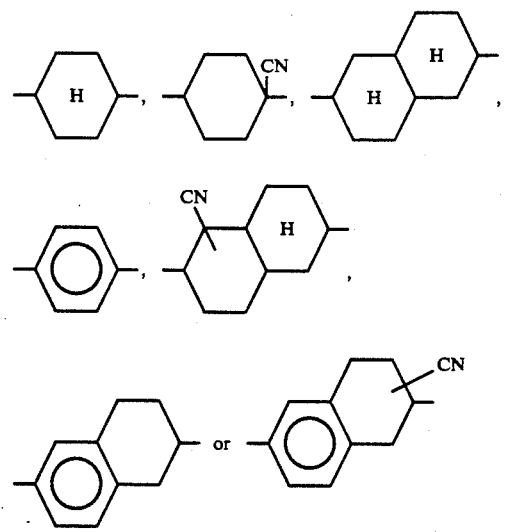

or one of these groups wherein one or more CH2 groups is/are replaced by 0 and/or S or aliphatic and/or aromatic CH groups are replaced by N, A° in each case independently of the other radicals A° is 1,4-cyclohexylene which is unsubstituted or mono- or polysubstituted by halogen, CH3 groups and/or nitrile groups, wherein one or two nonadjacent CH2 groups can also be replaced by —O— and/or —S— and/or a

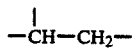

grouping can be replaced by

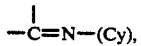

or 1,4-phenylene which is unsubstituted or mono- or polysubstituted by halogen atoms, CH3 groups and/or nitrile groups, wherein one or more CH groups can also be replaced by N (Ph), and one of the radicals A° is also 2,6-naphthylene (Na) or tetrahydro-2,6-naphthylene (4H-Na), optionally substituted by halogen or CN, Z° in each case independently of the other radicals Z° is —CO—O—, —O—CO—, -CH2—O—, —OCH2—, —CH2CH2— —CHCN—CH2—, —CH2—CHCN— or a single bond, and p is 1, 2 or 3, or in the case where A =tetra-or octahydrophenanthrene, also 0, wherein, in the case where A =

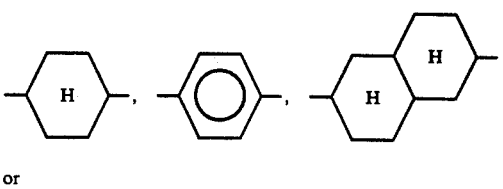

or

-continued

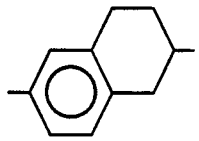

at least one group Z° is —CHCNCH₂— or —CH₂CHCN— and/or at least one CH₂ group in at least one of the groups R¹ and R² is replaced by —CHCN—.

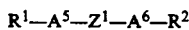

$$R^1-A^5-Z^1-A^6-R^2 \quad\quad III$$

wherein
R¹ and R2 each independently of one another are an alkyl group with in each case 1 to 15 C atoms, wherein one or more CH2 groups can also be replaced by a grouping chosen from the group comprising —O—, —S—, —CO—, —CH—halogen—, —CHCN—, —O—CO—, —O—COO—, —CO—O— and —CH=CH— or also by a combination of two suitable groupings, two hetero atoms not being linked directly to one another,
Z¹ is —CO—O—, —O—CO—, —CH₂CH₂—, —OCH₂—, —CH₂O— or a single bond and
A⁵ and A⁶ in each case independently of one another are trans-1,4-cyclohexylene, or 1,4-phenylene which is unsubstituted or substituted by fluorine.

$$R^3-(A^1-Z^1)_m-A-(Z^2-A^2)_n-R^4 \quad\quad IV$$

wherein
R³ and R⁴ in each case independently of one another are an alkyl group with in each case 1 to 15 C atoms, wherein one or more CH2 groups can also be replaced by a grouping chosen from the group comprising —O—, —S—, —CO—, —CH—halogen—, —CHCN—, —O—CO—, —O—COO—, —CO—O— and —CH=CH— or by a combination of two suitable groupings, two hetero atoms not being linked directly to one another, A¹ and A² in each case independently of one another are 1,4-cyclohexylene which is unsubstituted or mono- or polysubstituted by halogen atoms, CH3 groups and/or nitrile groups, wherein one or two non-adjacent CH2 groups can also be replaced by —O— and/or —S— and/or a

grouping can be replaced by

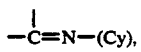

or 1,4-phenylene which is unsubstituted or mono- or polysubstituted by halogen atoms, CH3 groups and/or nitrile groups, wherein one or more CH groups can also be replaced by N (Ph), and one of the radicals A¹ and A² is also 2,6-naphthylene (Na) or tetrahydro-2,6-naphthylene (4H-Na), optionally substituted by halogen or CN,
A is 2-fluoro-1,4-phenylene, 2,3-difluoro-1,4-phenylene or 4,4'-biphenylyl which is mono-or polysubstituted in the 2-, 3-, 2'- and/or 3'-position by fluorine,
Z¹ and Z² are each —CO—O—, —O—CO—, —CH₂—CH₂—, —OCH₂—, —CH₂O— or a single bond,
m is 1 or 2 and
n is 0 or 1,
wherein, where m=2, the two groups A¹ and Z¹ can be identical or different from one another.

$$R^3-(A^3-Z^1)_o-Q^1-C\equiv C-Q^2-(Z^2-A^4)_p-R^4 \quad\quad V$$

wherein
R³ and R⁴ in each case independently of one another are an alkyl group with in each case 1 to 15 C atoms, wherein one or more CH2 groups can also be replaced by a grouping chosen from the group comprising —O—, —S—, —CO—, —CH—halogen—, —CHCN—, —O—CO—, —O—COO—, —CO—O— and —CH=CH— or also by a combination of two suitable groupings, two hetero atoms not being linked directly to one another,
Q¹ and Q² in each case independently of one another are 1,4-phenylene which is unsubstituted or mono- or polysubstituted by halogen atoms, CH3 groups and/or nitrile groups, and one of the groups Q¹ and Q2 is also pyridine-2,5-diyl,
A³ and A⁴ in each case independently of one another are trans-1,4-cyclohexylene, wherein one or two non-adjacent CH2 groups can also be replaced by —O— and/or —S—, or 1,4-phenylene, wherein one or more CH groups can also be replaced by N,
o and p in each case independently of one another are 0 or 1,
and Z¹ and Z² have the meaning given in the case of formula IV.

$$R^3-(A^1-Z^1)_m-A^1-C\equiv C-R^5 \quad\quad VI$$

wherein R⁵ is an alkyl group with 1 to 15 C atoms and R³, A¹, Z¹, Q¹ and m have the above mentioned meaning.

The media according to the invention are prepared in a manner which is customary per se. As a rule, the desired amount of the components used in a relatively small amount are dissolved in the component which makes up the main constituent, advantageously at elevated temperature. It is also possible to mix solutions of the components in an organic solvent, for example in acetone, chloroform or methanol, and to remove the solvent again, for example by distillation, after thorough mixing.

The dielectrics can also contain other additives which are known to the expert and are described in the literature. For example, 0-15% of pleochroic dyestuffs can be added, as well as conductive salts, preferably ethyldimethyldodecylammonium 4-hexoxybenzoate, tetrabutylammonium tetraphenylboranate or complex salts of crown ethers (compare, for example, Haller et al., Mcl. Cryst. Liq. Cryst. Volume 24, pages 249–258 (1973)), to improve the conductivity, or substances to modify the dielectric anisotropy, the viscosity and/or the orientation of the nematic phases. Such substances are described, for example, in DE-OS 2,209,127, 2,240,864, 2,321,632, 2,338,281, 2,450,088, 2,637,430 and 2,853,728.

The individual compounds of the formulae II to VI are either known or have preparation procedures which can easily be deduced from the prior art by the appropriate expert, since they are based on standard processes described in the literature.

The liquid crystal media according to the invention preferably consist of 2 to 15, preferably 3 to 18, components. As well as compounds of the formulae I to VI, other constituents can also additionally be present, for example in an amount of up to 45% of the total mixture, but preferably up to 34% and in particular up to 10%.

The media according to the invention preferably contain 1 to 40%, in particular 5 to 30% of the compounds according to the invention. Media containing more than 40%, in particular 45 to 90% of the compounds according to the invention, are further preferred. The media contain preferably 3, 4 or 5 compounds according to the invention. The content of the compounds of the formulae II to VI can be chosen in each case in a broad range to give totally 10 to 90%, in particular 20 to 80%.

The additional constituents mentioned above are preferably chosen from the nematic or nematogenic (monotropic or isotropic) substances; in particular from the classes of azoxybenzenes, benzylideneanilines, biphenyls, terphenyls, phenyl or cyclohexyl benzoates, phenyl or cyclohexyl cyclohexanecarboxylates, phenyl or cyclohexyl cyclohexylbenzoates, phenyl or cyclohexyl cyclohexylcyclohexanecarboxylates, cyclohexylphenylbenzoates, cyclohexylphenyl cyclohexanecarboxylates, cyclohexylphenyl cyclohexylcyclohexanecarboxylates, phenylcyclohexanes, cyclohexylbiphenyls, phenylcyclohexylcyclohexanes, cyclohexylcyclohexanes, cyclohexylcyclohexenes, cyclohexylcyclohexylcyclohexene, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenyl-cyclohexyl)ethanes, 1-cyclohexyl-2-biphenylethanes, 1-phenyl-2-cyclohexyl-phenylethanes, optionally halogenated stilbenes, benzyl phenyl ethers, tolanes and substituted cinnamic acids.

The 1,4-phenylene groups of these compounds may be fluorinated.

The most important compounds which are possible constituents of liquid crystal media according to the invention can be characterized by the formulae 1, 2, 3, 4 and 5:

  R'—L—U—R"  1

  R'—L—COO—U—R"  2

  R'—L—OOC—U—R"  3

  R'—L—CH$_2$CH$_2$—U—R"  4

  R'—L—C≡C—U—R"  5

In the formulae 1, 2, 3, 4 and 5 L and U may be equal or different from each other. L and U independently from each other denote a bivalent residue selected from the group consisting of -Phe-, -Cyc-, -Phe-Phe-, -Phe-Cyc-, -Cyc-Cyc-, -Pyr-, -Dio-, -G-Phe-, -G-Cyc- and their mirror images; in this compilation of residues Phe denotes unsubstituted or fluorinated 1,4-phenylene, Cyc trans- 1,4-cyclohexylene or 1,4-cyclohexenylene, Pyr pyrimidine-2,5-diyl or pyridine-2,5-diyl, Dio 1,3-dioxane-2,5-diyl and G 2-(trans-1,4-cyclohexyl)-ethyl, pyrimidine-2,5-diyl, pyridine-2,5-diyl or 1,3-dioxane-2,5-diyl.

One of the residues L and U is preferably Cyc, Phe or Pyr. U preferably denotes Cyc, Phe or Phe-Cyc. The liquid crystal media according to the invention preferably contain one or more components selected from the compounds of formulae 1, 2, 3, 4 and 5 with L and U meaning Cyc, Phe and Pyr, said liquid crystal media further containing at the same time one ore more components selected from the compounds of formulae 1, 2, 3, 4 and 5 with one of the residues L and U denoting Cyc, Phe and Pyr and the other residue being selected from the group consisting of -Phe-Phe-, -Phe-Cyc-, -Cyc-Cyc-, -G-Cyc-, said liquid crystal media containing in addition to this optionally one or more components selected from the compounds of formulae 1, 2, 3, 4 and 5 with L and U being selected from the group consisting of -Phe-Cyc-, -Cyc-Cyc-, -G-Phe- and -G-Cyc.

In a preferred subgroup of the compounds of formulae 1, 2, 3, 4 and 5 (subgroup 1) R' and R" are independently from each other alkyl, alkenyl, alkoxy, alkenoxy with up to 8 carbon atoms. R' and R" differ from one another in most of these compounds, one of the residues usually being alkyl or alkenyl. In another preferred subgroup of the compounds of formulae 1, 2, 3, 4 and 5 (subgroup 2) R" denotes -CN, -CF$_3$, -F, -Cl or -NCS while R' has the meaning indicated in subgroup 1 and is preferably alkyl or alkenyl. Other variants of the envisaged substituents in the compounds of formulae 1, 2, 3, 4 and 5 are also customary. Many such substances are commercially available. All these substances are obtainable by methods which are known from the literature or by analogous methods.

The liquid crystal media according to the invention preferably contain in addition to components selected from subgroup 1 also components of subgroup 2, the percentage of these components being as follows:

subgroup 1: 20 to 90%, in particular 30 to 90%
subgroup 2: 10 to 50%, in particular 10 to 50%

In these liquid crystal media the percentages of the compounds according to the invention and the compounds of subgroup 1 and 2 and further the compounds of the formulae II to VI may add up to give 100%.

The following examples are intended to illustrate the invention without limiting it. Percentages above and below are percentages by weight; all the temperatures are quoted in degree Celsius.

Further are: C: crystalline-solid state, S: smectic phase (the index denoting the type of smectic phase), N: nematic phase, Ch: cholesteric phase, I: isotropic phase. The number between two symbols indicates the transition temperature in degree Celsius.

Example 1

A mixture of 0.05 m 4-pentylphenyl boronic acid (obtained by reacting 4-pentylbiphenyl-4'-yl bromide with n-butyllithium and trimethylborate at low temperatures and subsequent hydrolyzing with HCl/H$_2$O), 0.05 m of 5-bromo-2-ethoxypyridine (obtained by reaction of 2,5-dibromopyridine with NaOC$_2$H$_5$), 1,25 g (0.001 m) of tetrakis (triphenylphosphine) palladium (Pd (Ph$_3$P)$_4$), 100 ml of toluene, 40 ml of ethanol and 50 ml of sodium carbonate solution (2 m) is stirred and refluxed for 3 hours. After cooling the organic layer is separated, washed with water and the solent evaporated. The crude 2-ethoxy-5-(4-pentylbiphenyl-4'-yl)pyridine is purified by chromatography on silica and/or crystallization.

The following compounds of the formulae VII and VIII arranged in the tables 1 and 2 are obtained analogously:

TABLE 1

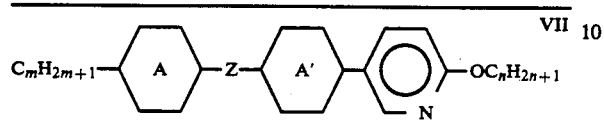
VII

| m | A | Z | A' | n |
|---|---|---|---|---|
| 2 | — | — | PheF | 2 |
| 3 | — | — | PheF | 2 |
| 4 | — | — | PheF | 2 |
| 5 | — | — | PheF | 1 |
| 6 | — | — | PheF | 1 |
| 2 | — | — | PheF | 3 |
| 3 | — | — | PheF | 3 |
| 4 | — | — | PheF | 3 |
| 5 | — | — | PheF | 4 |
| 7 | — | — | PheF | 5 |
| 5 | — | — | PheF | 8 |
| 2 | Phe | — | Phe | 2 |
| 3 | Phe | — | Phe | 3 |
| 3 | Phe | — | PheF | 3 |
| 4 | Phe | — | Phe | 3 |
| 5 | Phe | — | Phe | 4 |
| 6 | Cyc | — | Phe | 1 |
| 5 | Cyc | — | Phe | 2 |
| 4 | Cyc | — | Phe | 5 |
| 3 | Cyc | — | Phe | 7 |
| 4 | Cyc | — | PheF | 5 |
| 3 | Cyc | — | PheF | 5 |
| 2 | Cyc | — | Phe | 8 |
| 3 | Cyc | — | Phe | 6 |
| 2 | Cyc | — | PheF | 5 |
| 2 | PheF | — | Phe | 2 |
| 3 | PheF | — | Phe | 3 |
| 4 | PheF | — | Phe | 3 |
| 5 | PheF | — | Phe | 2 |
| 1 | Phe | —CH$_2$CH$_2$— | Phe | 8 |
| 2 | Phe | —CH$_2$CH$_2$— | Phe | 6 |
| 3 | Phe | —CH$_2$CH$_2$— | PheF | 5 |
| 4 | Phe | —CH$_2$CH$_2$— | Phe | 4 |
| 7 | Phe | —CH$_2$CH$_2$— | PheF | 3 |
| 3 | Phe | —CH$_2$CH$_2$— | Phe | 2 |
| 5 | Phe | —CH$_2$CH$_2$— | Phe | 1 |
| 2 | Phe | —C≡C— | Phe | 2 |
| 3 | Phe | —C≡C— | Phe | 2 |
| 4 | Phe | —C≡C— | PheF | 3 |
| 5 | Phe | —C≡C— | PheF | 4 |
| 8 | Phe | —C≡C— | Phe | 2 |
| 6 | PheF | —C≡C— | Phe | 2 |
| 4 | PheF | —C≡C— | Phe | 3 |
| 3 | PheF | —C≡C— | Phe | 2 |
| 2 | Cyc | —C≡C— | Phe | 3 |
| 3 | Cyc | —C≡C— | Phe | 3 |
| 4 | Cyc | —C≡C— | Phe | 5 |
| 3 | Cyc | —C≡C— | PheF | 4 |
| 5 | Cyc | —C≡C— | Phe | 2 |
| 4 | Cyc | —C≡C— | PheF | 3 |
| 2 | Cyc | —CH$_2$CH$_2$— | Phe | 3 |
| 3 | Cyc | —CH$_2$CH$_2$— | Phe | 4 |
| 4 | Cyc | —CH$_2$CH$_2$— | Phe | 5 |
| 5 | Cyc | —CH$_2$CH$_2$— | Phe | 3 |
| 7 | Cyc | —CH$_2$CH$_2$— | Phe | 2 |
| 2 | Pyd | —C≡C— | Phe | 3 |
| 3 | — | — | Pyd | 4 |
| 8 | — | — | Pyd | 8 |
| 4 | Cyc | —CH$_2$CH$_2$— | PheF | 5 |
| 2 | Cyc | —CH$_2$CH$_2$— | PheF | 6 |
| 3 | Cyc | —CH$_2$CH$_2$— | PheF | 2 |
| 3 | Pyd | —C≡C— | Phe | 2 |
| 4 | Pyr | —C≡C— | Phe | 2 |
| 2 | Pyr | —C≡C— | Phe | 4 |
| 1 | Pyd | —CH$_2$CH$_2$— | Phe | 2 |
| 5 | Pyd | —CH$_2$CH$_2$— | Phe | 3 |

TABLE 1-continued

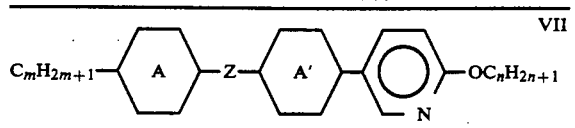
VII

| m | A | Z | A' | n |
|---|---|---|---|---|
| 6 | Pyr | —CH$_2$CH$_2$— | Phe | 3 |
| 2 | Pyr | —CH$_2$CH$_2$— | Phe | 8 |
| 2 | PheF | —CH$_2$CH$_2$— | Phe | 2 |
| 2 | PheF | —CH$_2$CH$_2$— | Phe | 3 |
| 3 | PheF | —CH$_2$CH$_2$— | Phe | 5 |

Further combination of m and n are certainly possible and such compounds are obtained analogously.

TABLE 2

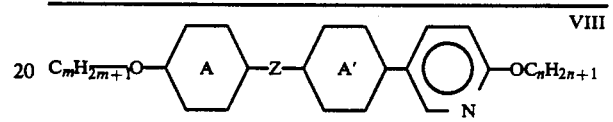
VIII

| m | A | Z | A' | n |
|---|---|---|---|---|
| 2 | — | — | Phe | 2 |
| 3 | — | — | Phe | 2 |
| 4 | — | — | Phe | 2 |
| 5 | — | — | PheF | 2 |
| 6 | — | — | PheF | 2 |
| 2 | — | — | Phe | 3 |
| 3 | — | — | PheF | 3 |
| 3 | — | — | Phe | 4 |
| 4 | — | — | Phe | 3 |
| 4 | — | — | PheF | 5 |
| 5 | — | — | Phe | 4 |
| 7 | — | — | Phe | 3 |
| 8 | — | — | Phe | 8, C 50° S$_B$ 69° S$_A$ 80° I |
| 8 | — | — | ![F-phenyl] | 8, C 41°, S$_A$ 49° I |
| 2 | — | — | Pyd | 3 |
| 8 | — | — | Pyd | 8, C 49° S$_A$ 55° I |
| 3 | — | — | Pyd | 5 |
| 5 | — | — | Pyr | 2 |
| 7 | — | — | Pyr | 3 |
| 2 | Phe | — | Phe | 3 |
| 3 | Phe | — | Phe | 4 |
| 3 | Phe | — | PheF | 4 |
| 4 | Phe | — | Phe | 3 |
| 5 | Phe | — | Phe | 2 |
| 5 | Phe | — | PheF | 2 |
| 6 | Phe | — | Phe | 1 |
| 2 | Cyc | — | Phe | 3 |
| 3 | Cyc | — | Phe | 3 |
| 4 | Cyc | — | Phe | 2 |
| 5 | Cyc | — | Phe | 2 |
| 2 | Cyc | — | Phe | 5 |
| 2 | Cyc | — | PheF | 5 |
| 7 | Cyc | — | Phe | 2 |
| 3 | Cyc | — | PheF | 2 |
| 2 | Cyc | —C≡C— | Phe | 2 |
| 3 | Cyc | —C≡C— | Phe | 2 |
| 5 | Cyc | —C≡C— | Phe | 3 |
| 3 | PheF | — | Phe | 5 |
| 6 | PheF | — | Phe | 2 |
| 4 | PheF | — | Phe | 4 |
| 2 | Phe | —CH$_2$CH$_2$— | Phe | 7 |
| 3 | Phe | —CH$_2$CH$_2$— | Phe | 5 |
| 4 | Phe | —CH$_2$CH$_2$— | Phe | 2 |
| 3 | Phe | —CH$_2$CH$_2$— | PheF | 3 |
| 4 | Phe | —CH$_2$CH$_2$— | Phe | 5 |
| 8 | Phe | —CH$_2$CH$_2$— | PheF | 8 |
| 2 | Phe | —C≡C— | Phe | 2 |

TABLE 2-continued

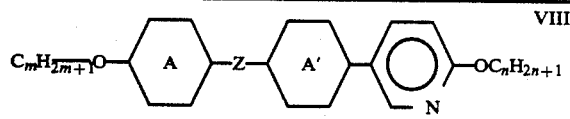
(VIII)

| m | A | Z | A' | n |
|---|------|-----------|------|---|
| 3 | Phe  | —C≡C—     | Phe  | 4 |
| 4 | PheF | —CH₂CH₂—  | Phe  | 2 |
| 1 | PheF | —CH₂CH₂—  | Phe  | 6 |
| 8 | Phe  | —C≡C—     | Phe  | 1 |
| 4 | Phe  | —C≡C—     | Phe  | 5 |
| 2 | PheF | —C≡C—     | Phe  | 2 |
| 3 | Phe  | —C≡C—     | PheF | 3 |
| 4 | Phe  | —C≡C—     | PheF | 2 |
| 2 | Cyc  | —C≡C—     | PheF | 3 |
| 5 | Cyc  | —C≡C—     | PheF | 2 |
| 4 | Cyc  | —C≡C—     | Phe  | 1 |
| 2 | Cyc  | —CH₂CH₂—  | Phe  | 3 |
| 3 | Cyc  | —CH₂CH₂—  | Phe  | 3 |
| 4 | Cyc  | —CH₂CH₂—  | Phe  | 2 |
| 5 | Cyc  | —CH₂CH₂—  | Phe  | 2 |
| 4 | Cyc  | —CH₂CH₂—  | PheF | 3 |
| 2 | Cyc  | —CH₂CH₂—  | PheF | 4 |
| 3 | Pyd  | —CH₂CH₂—  | Phe  | 4 |
| 2 | Pyd  | —C≡C—     | Phe  | 5 |
| 5 | Pyr  | —C≡C—     | Phe  | 2 |
| 4 | Pyr  | —CH₂CH₂—  | Phe  | 3 |

Further combinations of m and n are certainly possible and such compounds are obtained analogously.

EXAMPLE 2

0.05 m of ethylmagnesium bromide in ether are added to a mixture of 0.05 m of 4-propylphenylacetylene at 0°-10°. The mixture is stirred for 4 hours at room temperature and then a solution of 0.05 m of 2-ethoxy-5-bromopyridine and 0.5 g of NiCl₂(Ph₃P)₂ in ether is added. After stirring for 6 hours at room temperature and customary work-up 1-(4-propylphenyl)-2-(2-ethoxy-pyridine-5-yl)-acetylene is obtained.

The following compounds of the formulae IX and X listed in the table 3 are obtained analogously, whereby further combinations of m and n are certainly possible.

TABLE 3

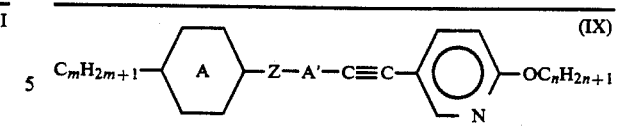
(IX)

and

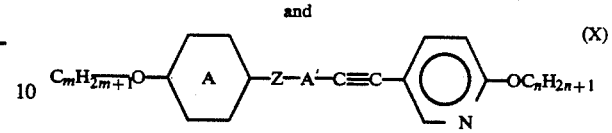
(X)

| m | A    | Z        | A'   | n |
|---|------|----------|------|---|
| 2 | —    | —        | Phe  | 2 |
| 2 | —    | —        | Phe  | 3 |
| 3 | —    | —        | Phe  | 2 |
| 3 | —    | —        | Phe  | 3 |
| 4 | —    | —        | Phe  | 5 |
| 5 | —    | —        | Phe  | 4 |
| 5 | —    | —        | Phe  | 2 |
| 2 | Cyc  | —        | Phe  | 5 |
| 3 | Cyc  | —        | Phe  | 2 |
| 4 | Cyc  | —        | Phe  | 3 |
| 2 | Cyc  | —        | Phe  | 8 |
| 2 | —    | —        | Cyc  | 3 |
| 3 | —    | —        | Cyc  | 4 |
| 4 | —    | —        | Cyc  | 2 |
| 6 | —    | —        | Cyc  | 2 |
| 2 | Cyc  | —        | Cyc  | 3 |
| 3 | Cyc  | —        | Cyc  | 4 |
| 4 | Cyc  | —        | Cyc  | 5 |
| 5 | Cyc  | —        | Cyc  | 2 |
| 4 | Phe  | —        | Phe  | 5 |
| 8 | Phe  | —        | Phe  | 1 |
| 5 | Phe  | —        | Phe  | 3 |
| 2 | PheF | —        | Phe  | 4 |
| 3 | PheF | —        | Phe  | 2 |
| 2 | Phe  | —CH₂CH₂— | Phe  | 3 |
| 3 | Phe  | —CH₂CH₂— | Phe  | 5 |
| 5 | PheF | —CH₂CH₂— | Phe  | 2 |
| 4 | Phe  | —CH₂CH₂— | Phe  | 6 |
| 2 | Cyc  | —CH₂CH₂— | Phe  | 3 |
| 4 | Phe  | —        | Cyc  | 5 |
| 3 | Phe  | —        | Cyc  | 2 |

EXAMPLE 3

Hydrogenation of 1-(4-propylbiphenyl-4'-yl)-2-(2-ethoxypyridine-5-yl)acetylene in THF in the presence of PD-C at room temperature and under normal pressure yields after customary work-up 1-(4-propylbiphenyl-4'-yl)-2-(2-ethoxypyridine-5-yl)ethane.

The following compounds of the formulae XI and XII listed in- the table 4 are obtained analogously ad further compounds having different combinations of m and n are certainly obtainable analogously.

TABLE 4

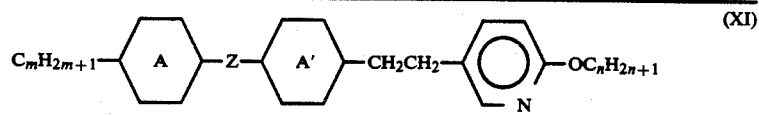
(XI)

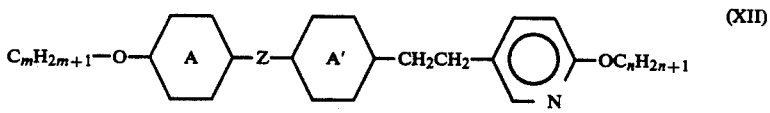
(XII)

| m | A | Z | A'   | n |
|---|---|---|------|---|
| 2 | — | — | Phe  | 2 |
| 2 | — | — | Phe  | 3 |
| 3 | — | — | Phe  | 2 |
| 3 | — | — | PheF | 2 |
| 3 | — | — | Phe  | 3 |
| 4 | — | — | PheF | 3 |

TABLE 4-continued $$C_mH_{2m+1}-\boxed{A}-Z-\boxed{A'}-CH_2CH_2-\boxed{\underset{N}{\bigcirc}}-OC_nH_{2n+1} \quad (XI)$$

$$C_mH_{2m+1}-O-\boxed{A}-Z-\boxed{A'}-CH_2CH_2-\boxed{\underset{N}{\bigcirc}}-OC_nH_{2n+1} \quad (XII)$$

| m | A | Z | A' | n |
|---|---|---|---|---|
| 4 | — | — | Phe | 5 |
| 5 | — | — | Phe | 4 |
| 5 | — | — | Phe | 2 |
| 2 | Cyc | — | Phe | 5 |
| 3 | Cyc | — | Phe | 3 |
| 4 | Cyc | — | Phe | 2 |
| 2 | Cyc | — | Phe | 7 |
| 2 | — | — | Cyc | 2 |
| 3 | — | — | Cyc | 2 |
| 4 | — | — | Cyc | 3 |
| 5 | — | — | Cyc | 4 |
| 6 | — | — | Cyc | 5 |
| 3 | Cyc | — | Cyc | 2 |
| 2 | Cyc | — | Cyc | 4 |
| 4 | Cyc | — | Cyc | 3 |
| 5 | Cyc | — | Cyc | 2 |
| 2 | Cyc | — | Cyc | 8 |
| 2 | Phe | — | Phe | 1 |
| 3 | Phe | — | Phe | 4 |
| 5 | Phe | — | Phe | 2 |
| 4 | Phe | — | Phe | 3 |
| 3 | PheF | — | Phe | 2 |
| 6 | PheF | — | Phe | 3 |
| 3 | Phe | —CH$_2$CH$_2$— | Phe | 2 |
| 4 | Phe | —CH$_2$CH$_2$— | Phe | 5 |
| 2 | PheF | —CH$_2$CH$_2$— | Phe | 7 |
| 5 | PheF | —CH$_2$CH$_2$— | Phe | 2 |
| 2 | Cyc | —CH$_2$CH$_2$— | Phe | 2 |
| 3 | Cyc | —CH$_2$CH$_2$— | Cyc | 5 |
| 3 | Phe | — | Cyc | 2 |
| 2 | Phe | — | Cyc | 4 |

EXAMPLE 4

5-(4-Ethylphenyl)-pyridine-2-yl-(trans-4-propylcyclohexylmethyl)ether is obtained analogously to example 1 by reacting 4-ethylphenyl boronic acid with 5-bromo-2-(trans-4-propylcyclohexylmethyloxy)-pyridine.

The following compounds of the formulae XIII and XIV arranged in table 5 are obtained analogously.

TABLE 5

$$C_mH_{2m+1}-\boxed{A}-Z-\boxed{A'}-\boxed{\underset{N}{\bigcirc}}-OCH_2-Cyc-C_nH_{2n+1} \quad (XIII)$$

$$C_mH_{2m+1}-O-\boxed{A}-Z-\boxed{A'}-\boxed{\underset{N}{\bigcirc}}-OCH_2-Cyc-C_nH_{2n+1} \quad (XIV)$$

| m | A | Z | A' | n |
|---|---|---|---|---|
| 2 | — | — | Phe | 2 |
| 2 | — | — | Phe | 3 |
| 2 | — | — | Phe | 4 |
| 2 | — | — | Phe | 5 |
| 3 | — | — | Phe | 4 |
| 4 | — | — | Phe | 2 |
| 5 | — | — | Phe | 2 |
| 2 | Cyc | — | Phe | 4 |
| 3 | Cyc | — | Phe | 2 |
| 5 | Cyc | — | Phe | 4 |
| 2 | Phe | — | Phe | 5 |
| 3 | Phe | —CH$_2$CH$_2$— | Phe | 5 |
| 5 | Phe | — | Phe | 3 |
| 2 | Phe | —C≡C— | Phe | 8 |

TABLE 5-continued $$C_mH_{2m+1}-\underset{}{\boxed{A}}-Z-\underset{}{\boxed{A'}}-\underset{N}{\boxed{\phantom{X}}}-OCH_2-Cyc-C_nH_{2n+1} \quad \text{(XIII)}$$

$$C_mH_{2m+1}-O-\underset{}{\boxed{A}}-Z-\underset{}{\boxed{A'}}-\underset{N}{\boxed{\phantom{X}}}-OCH_2-Cyc-C_nH_{2n+1} \quad \text{(XIV)}$$

| m | A | Z | A' | n |
|---|---|---|----|---|
| 4 | Phe | — | Phe | 3 |
| 2 | Cyc | —CH₂CH₂— | Phe | 5 |
| 6 | Cyc | —CH₂CH₂— | Phe | 2 |

The definitions of m and n in Table 5 may be combined at discretion.

EXAMPLE 5

0.02 m of trans-4-(trans-4-propylcyclohexyl)-cyclohexylbromide, 0.04 m of lithium, 0.01 m of ZnBr₂, 40 ml of toluene and 12 ml of THF are stirred at 0°-10° for 2 hours under ultrasonic. The 0.02 m of 5-bromo-2-ethoxy-pyridine and 0.5 g Pd (Ph₃P)₄ as the catalyst are added, and the mixture is stirred for further 4 hours at room temperature. Customary work-up yields 2-ethoxy-5-[trans-4-(trans-4-propylcyclohexyl)cyclohexyl]-pyridine.

The following compounds of the formula XV listed in table 6, the formula XVI listed in table 7 and the formula XVIII in table 8 are obtained analogously.

The definitions of m and n in these tables may be combined at discretion.

TABLE 6

$$C_mH_{2m+1}-(Cyc-Z)_r-Cyc-\underset{N}{\boxed{\phantom{X}}}-OC_nH_{2n+1} \quad \text{(XV)}$$

| m | A | Z | n |
|---|---|---|---|
| 2 | 0 | — | 2 |
| 3 | 0 | — | 3 |
| 2 | 0 | — | 3 |
| 4 | 0 | — | 3 |
| 5 | 0 | — | 4 |
| 5 | 0 | — | 2 |
| 2 | 0 | — | 5 |
| 2 | 0 | — | 8 |
| 8 | 0 | — | 2 |
| 3 | 0 | — | 2 |
| 2 | 1 | — | 3 |
| 3 | 1 | — | 4 |
| 4 | 1 | — | 3 |
| 5 | 1 | — | 2 |
| 7 | 1 | — | 2 |
| 2 | 1 | — | 4 |
| 2 | 1 | — | 5 |
| 2 | 1 | —CH₂CH₂— | 3 |
| 2 | 1 | —CH₂CH₂— | 2 |
| 5 | 1 | —CH₂CH₂— | 3 |
| 4 | 1 | —C≡C— | 3 |
| 3 | 1 | —C≡C— | 2 |
| 2 | 1 | —C≡C— | 5 |
| 2 | 1 | —C≡C— | 8 |

TABLE 7

$$C_mH_{2m+1}-O-\left\{\underset{}{\boxed{\phantom{X}}}-Z\right\}_r-Cyc-\underset{N}{\boxed{\phantom{X}}}-OC_nH_{2n+1} \quad \text{(XVI)}$$

| m | r | Z | n |
|---|---|---|---|
| 2 | 1 | — | 2 |
| 2 | 1 | — | 3 |
| 3 | 1 | — | 2 |
| 4 | 1 | — | 3 |
| 5 | 1 | — | 2 |
| 2 | 1 | — | 5 |
| 3 | 1 | — | 4 |
| 4 | 1 | —CH₂CH₂— | 2 |
| 3 | 1 | —CH₂CH₂— | 3 |
| 2 | 1 | —CH₂CH₂— | 5 |
| 3 | 1 | —C≡C— | 2 |
| 4 | 1 | —C≡C— | 3 |
| 5 | 1 | —C≡C— | 4 |

TABLE 8

$$C_mH_{2m+1}-Cyc-\underset{N}{\boxed{\phantom{X}}}-OCH_2-Cyc-C_nH_{2n+1} \quad \text{(XVII)}$$

| m | 2 2 3 4 3 5 2 2 3 4 8 3 5 6 2 4 |
|---|---|
| n | 2 3 2 5 4 2 8 7 3 7 2 5 4 2 7 3 |

EXAMPLE 6 a) 0.6 m of n-butyllithium are added to 0.6 m of diisopropylamine in 600 ml of THF at −10°. Then the mixture is cooled to −60° to −70° and 0.6 m of 2,6-difluoropyridine are added. The mixture is stirred for further 15 minutes and 0.6 m of trimethylborate is added at −60°. The mixture is allowed to warm to −30° and is hydrolyzed by addition of 170 ml of HCl (25%) and 100 ml of H₂O. Ether is added and after customary work-up 2,6-difluoropyridine-3-boronic acid is obtained.

b) A mixture of 0.05 m of 4-(trans-4-pentylcyclohexyl)bromobenzene, 0.06 m of 2,6-difluoropyridine-5-boronic acid, 100 ml of toluene, 40 ml of ethanol, 1.25 g of Pd(Ph₃P)₄ and 50 ml of a solution of Na₂CO₃ (2 m) is stirred and heated for hours at 60°. After customary work-up and recrystallization from ethanol 2,6-difluoro-3-[4-(trans-4-pentylcyclohexyl)phenyl]pyridine with C 58° N 107° I is obtained.

c) 0.06 m of NaH is added to a suspension of 0.06 m of ethanol in 50 ml THF at 20-25°. When the gas development has finished 0.03 m of the above 2,6-difluoropyridine derivative is added. After 15 minutes the mixture is poured in 150 ml of H20, extracted with petroleum ether and worked up as usual. Recrystallization from methanol/ethanol yields 6-ethoxy-2-fluoro-3-[trans-4-pentylcyclohexyl)phenyl)pyridine with C 72° N 147.3° I.

The following compounds of the formulae XVIII and XIX listed in the tables 9 and 10 are obtained analogously. The definitions of m and n in these tables may be combined at discretion in order to obtain further compounds of these types.

TABLE 9

$C_mH_{2m+1}$—A—Z—A'—(pyridine with F)—O—$(CH_2-Cyc)_S$—$C_nH_{2n+1}$    XVIII

| m | A | Z | A' | S | n |
|---|---|---|----|---|---|
| 2 | Cyc | — | Phe | 0 | 2 |
| 3 | Cyc | — | Phe | 0 | 2 |
| 4 | Cyc | — | Phe | 0 | 2 |
| 5 | Cyc | — | Phe | 0 | 3 |
| 4 | Cyc | — | Phe | 0 | 4 |
| 2 | Cyc | — | Phe | 1 | 5 |
| 3 | Cyc | — | Phe | 1 | 2 |
| 2 | — | — | Phe | 0 | 2 |
| 2 | — | — | Phe | 0 | 3 |
| 6 | — | — | Phe | 0 | 2 |
| 3 | — | — | Pyd | 0 | 5 |
| 8 | — | — | Pyd | 0 | 2 |
| 4 | — | — | Pyr | 0 | 3 |
| 2 | — | — | Pyr | 0 | 8 |
| 2 | Phe | — | Phe | 0 | 3 |
| 3 | Phe | — | Phe | 0 | 2 |
| 7 | Phe | — | Phe | 0 | 3 |
| 2 | Phe | — | Phe | 0 | 5 |
| 3 | PheF | — | Phe | 0 | 4 |
| 5 | Phe | — | PheF | 0 | 2 |
| 4 | Phe | — | Phe | 1 | 2 |
| 2 | Phe | — | Phe | 1 | 5 |
| 3 | — | — | Phe | 1 | 6 |
| 4 | — | — | Phe | 1 | 5 |
| 3 | — | — | Phe | 1 | 2 |
| 2 | Cyc | —CH$_2$CH$_2$— | Phe | 0 | 2 |
| 2 | Cyc | —CH$_2$CH$_2$— | Phe | 0 | 8 |
| 4 | Cyc | —CH$_2$CH$_2$— | Phe | 0 | 5 |
| 3 | Cyc | —C≡C— | Phe | 0 | 4 |
| 6 | Cyc | —C≡C— | Phe | 0 | 1 |
| 8 | Phe | —CH$_2$CH$_2$— | Phe | 0 | 2 |
| 5 | Phe | —CH$_2$CH$_2$— | Phe | 0 | 4 |
| 3 | PheF | —CH$_2$CH$_2$— | Phe | 0 | 2 |
| 4 | Phe | —CH$_2$CH$_2$— | PheF | 0 | 5 |
| 2 | Phe | —C≡C— | Phe | 0 | 3 |
| 3 | Phe | —C≡C— | Phe | 0 | 3 |
| 4 | PheF | —C≡C— | Phe | 0 | 3 |

TABLE 10

$C_mH_{2m+1}$—O—A—Z—A'—(pyridine with F)—O—$(CH_2Cyc)_S$—$C_nH_{2n+1}$    XIX

| m | A | Z | A' | S | n |
|---|---|---|----|---|---|
| 2 | — | — | Phe | 0 | 4 |
| 4 | — | — | Phe | 0 | 2 |
| 3 | — | — | Phe | 0 | 3 |
| 8 | — | — | Phe | 0 | 8 |
| 3 | — | — | Pyd | 0 | 2 |
| 5 | — | — | Pyd | 0 | 3 |
| 4 | — | — | Pyr | 0 | 2 |
| 6 | — | — | Pyr | 0 | 3 |
| 2 | Phe | — | Phe | 0 | 5 |
| 2 | Phe | — | Phe | 0 | 2 |
| 1 | Phe | — | Phe | 0 | 7 |
| 4 | Phe | — | Phe | 0 | 3 |
| 5 | PheF | — | Phe | 0 | 2 |
| 3 | Phe | — | PheF | 0 | 4 |

TABLE 10-continued

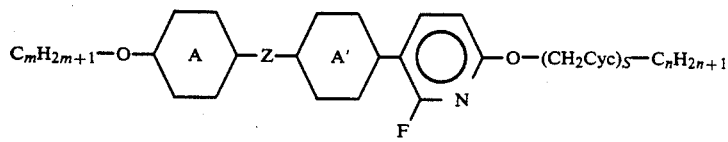
XIX

| m | A | Z | A' | S | n |
|---|---|---|---|---|---|
| 3 | Phe | — | Phe | 1 | 5 |
| 2 | Phe | — | Phe | 1 | 6 |
| 3 | — | — | Phe | 1 | 5 |
| 4 | — | — | Phe | 1 | 3 |
| 7 | — | — | Phe | 1 | 2 |
| 5 | Phe | —$CH_2CH_2$— | Phe | 0 | 2 |
| 4 | Phe | —$CH_2CH_2$— | Phe | 0 | 2 |
| 3 | Phe | —$CH_2CH_2$— | Phe | 0 | 3 |
| 2 | Phe | —$CH_2CH_2$— | Phe | 0 | 3 |
| 4 | Phe | —C≡C— | Phe | 0 | 4 |
| 4 | PheF | —C≡C— | Phe | 0 | 2 |
| 3 | Phe | —C≡C— | PheF | 0 | 5 |
| 8 | PheF | —$CH_2CH_2$— | Phe | 0 | 8 |
| 4 | Phe | —$CH_2CH_2$— | Phe | 0 | 2 |

EXAMPLE 7 a) Analogously to example 6 a) 2,6-difluoropyridine is reacted with lithiumdiisopropylamide. Then $J_2$ is added to the mixture at −60° to −70° and customary work-up yields 2,6-difluoro-3-iodopyridine.

b) 0.2 mM of $PdCl_2(Pb_3P)_2$ and 0.1 m of CuJ are added to a suspension of 0.01 M of 2,6-difluoro-3-iodopyridine, 0.01 M of 4-pentylphenylacetylene and 200 ml of triethylamine.

The mixture is stirred for 8 hours at room temperature and customary work-up yields 1-(4-pentylphenyl)-2-(2,6-difluoropyridine-3yl)-acetylene.

This compound is transferred into 1(4-pentylphenyl)-2-(6-ethoxy-2-fluoropyridine-3-yl)-acetylene analogously to example 6 c).

The following compounds of the formulae XX and XXI listed in the table 11 are obtained analogously. The definitions of m and n may be combined at discretion.

TABLE 11

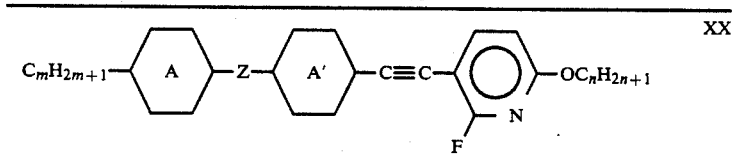
XX

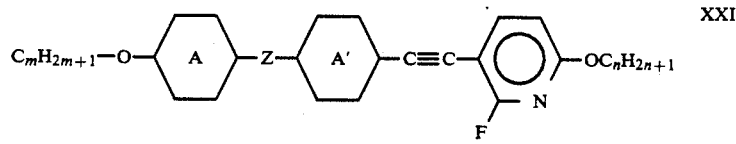
XXI

| m | A | Z | A' | n |
|---|---|---|---|---|
| 2 | — | — | Phe | 2 |
| 3 | — | — | Phe | 5 |
| 4 | — | — | Phe | 2 |
| 5 | — | — | Phe | 3 |
| 2 | Phe | — | Phe | 3 |
| 6 | Phe | — | Phe | 2 |
| 5 | Phe | — | Phe | 4 |
| 3 | — | — | PheF | 2 |
| 4 | PheF | — | Phe | 5 |
| 2 | PheF | — | Phe | 8 |
| 4 | Cyc | — | Phe | 2 |
| 3 | Cyc | — | Phe | 4 |
| 5 | Cyc | — | Phe | 5 |
| 7 | Cyc | — | Phe | 2 |
| 3 | Cyc | — | Phe | 6 |
| 2 | Phe | —$CH_2CH_2$— | Phe | 5 |
| 3 | Phe | —$CH_2CH_2$— | Phe | 4 |
| 5 | Cyc | —$CH_2CH_2$— | Phe | 2 |
| 4 | Cyc | —$CH_2CH_2$— | Phe | 3 |
| 3 | PheF | —$CH_2CH_2$— | Phe | 2 |
| 2 | Phe | —C≡C— | Phe | 5 |
| 3 | Cyc | —C≡C— | Phe | 2 |

EXAMPLE 8

Analogously to example 3 1-(4-pentylphenyl)-2-(6-ethoxy-2-fluoropyridine-3-yl)-acetylene is hydrogenated to obtain 1-(4-pentylphenyl)-1-(6-ethoxy-2-fluoropyridine-3-yl)ethane.

The following compounds of the formulae XXII and XXIII listed in table 12 are obtained analogously. The definitions of m and n may be combined at discretion.

TABLE 12

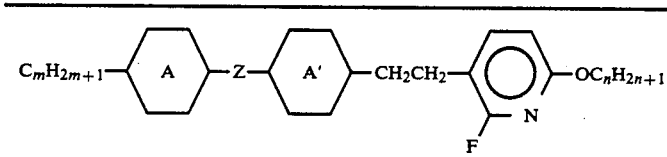
XXII

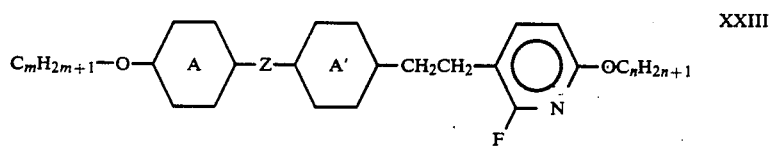
XXIII

| m | A | Z | A' | n |
|---|---|---|-----|---|
| 2 | — | — | Phe | 3 |
| 4 | — | — | Phe | 2 |
| 3 | — | — | PheF | 3 |
| 5 | — | — | Phe | 4 |
| 3 | Phe | — | Phe | 5 |
| 4 | Phe | — | Phe | 7 |

EXAMPLE 9

Analogously to example 5 2,6-difluoro-3-[trans-4-(trans-4-propylcyclohexyl)cyclohexyl]pyridine is obtained by reacting 2,6-difluoro-3-iodopyridine with trans-4-(trans-4propylcyclohexyl)cyclohexylbromide. 6-Ethoxy-2-fluoro-3-[trans-4-(trans-4-propylcyclohexyl)cyclohexyl]pyridine is then obtained analogously to example 6 c).

The following compounds of the formulae XXIV and XXV listed in the tables 13 and 14 are obtained analogously. The definitions of m and n may be combined at discretion.

TABLE 13

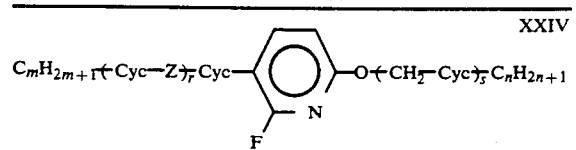
XXIV

| m | r | Z | s | n |
|---|---|---|---|---|
| 2 | 0 | — | 0 | 2 |
| 4 | 0 | — | 0 | 2 |
| 3 | 0 | — | 0 | 3 |
| 2 | 0 | — | 0 | 5 |
| 3 | 0 | — | 1 | 2 |
| 5 | 0 | — | 1 | 3 |
| 4 | 0 | — | 1 | 5 |
| 2 | 1 | — | 0 | 2 |
| 2 | 1 | — | 0 | 6 |
| 3 | 1 | — | 0 | 4 |
| 5 | 1 | — | 0 | 2 |
| 7 | 1 | — | 0 | 3 |
| 4 | 1 | — | 1 | 5 |
| 2 | 1 | — | 1 | 7 |
| 3 | 1 | —CH$_2$CH$_2$— | 0 | 4 |
| 5 | 1 | —CH$_2$CH$_2$— | 0 | 5 |
| 2 | 1 | —CH$_2$CH$_2$— | 0 | 3 |
| 4 | 1 | —C≡C— | 0 | 2 |
| 5 | 1 | —C≡C— | 0 | 3 |
| 2 | 1 | —C≡C— | 0 | 5 |

TABLE 14

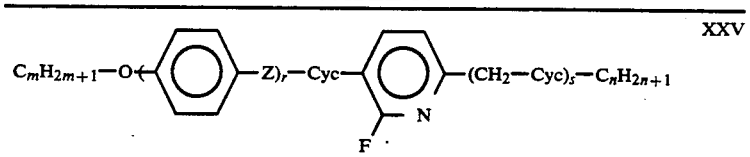
XXV

| m | r | Z | A' | n |
|---|---|---|----|---|
| 2 | 1 | — | 0 | 2 |
| 2 | 1 | — | 0 | 3 |
| 3 | 1 | — | 0 | 5 |
| 4 | 1 | — | 0 | 4 |
| 5 | 1 | — | 1 | 3 |
| 3 | 1 | — | 1 | 4 |
| 7 | 1 | —CH$_2$CH$_2$— | 0 | 2 |
| 8 | 1 | —CH$_2$CH$_2$— | 0 | 8 |
| 2 | 1 | —CH$_2$CH$_2$— | 1 | 3 |
| 3 | 1 | —C≡C— | 0 | 2 |
| 5 | 1 | —C≡C— | 0 | 4 |

TABLE 14-continued

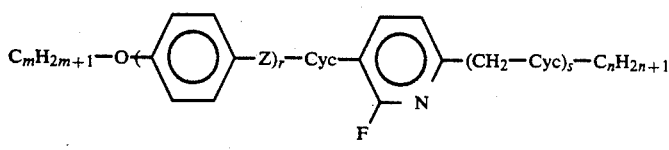
XXV

| m | r | Z | A' | n |
|---|---|------|---|---|
| 4 | 1 | —C≡C— | 0 | 5 |

EXAMPLE 10

A liquid crystalline medium consisting of
a) 90% of a mixture N consisting of
22% trans-1-p-ethylphenyl-4-propylcyclohexane,
20% trans-1-p-methoxyphenyl-4-propylcylohexane,
15% trans-1-p-ethoxyphenyl-4-propylcyclohexane,
19% 4-ethyl-4'-(trans-4-propylcyclohexyl)biphenyl,
14% 4-ethyl-4'-(trans-4-pentylcyclohexyl) biphenyl,
5% 4-(trans-4-pentylcyclohexyl)-4'-(trans-4-propylcyclohexyl)biphenyl,
and
5% 4,4=-bis-(trans-4-propylcyclohexyl) biphenyl
and
b) 10% of 2-octyloxy-5-(3-fluoro-4-octyloxyphenyl)-pyridine
has a clearing point of 65.3°, Δε= —0.06 and the viscosity is 14.3 mmz/sec at 20°.

EXAMPLE 11

A liquid crystalline medium consisting of
a) 90% of a mixture N (described in example 10) and
b) 10% of 2-octyloxy-5-(4-octyloxyphenyl)-pyridine
has a viscosity of 14.3 mm²/sec at 20° and a clearing point of 69.5°.

We claim:
1. A pyridine derivative of the Formulae Ia-Ir:

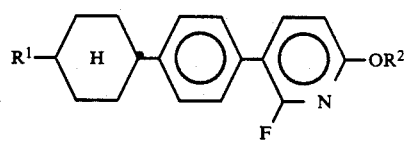
Ia

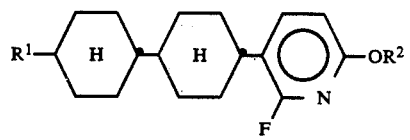
Ib

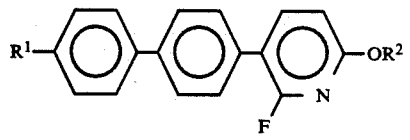
Ic

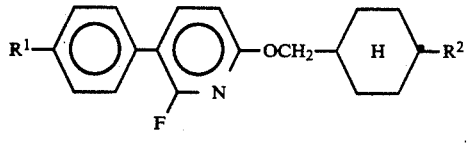
Id

-continued

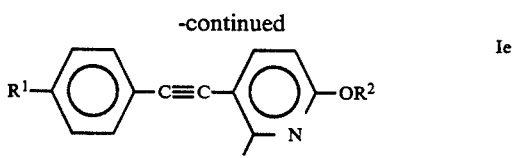
Ie

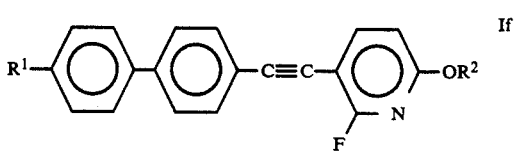
If

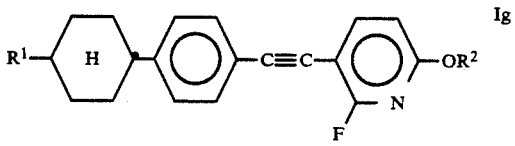
Ig

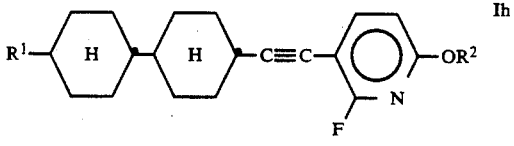
Ih

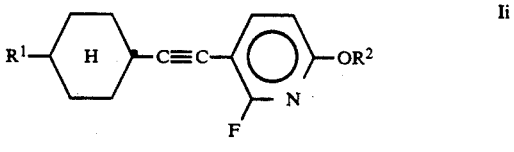
Ii

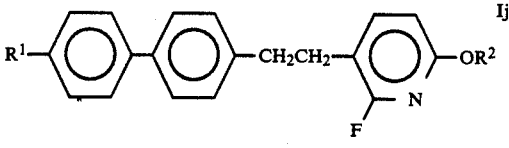
Ij

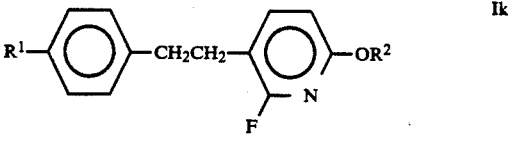
Ik

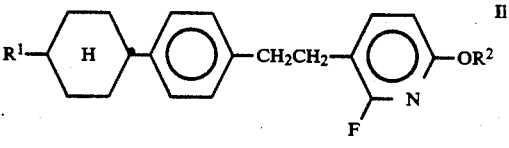
Il

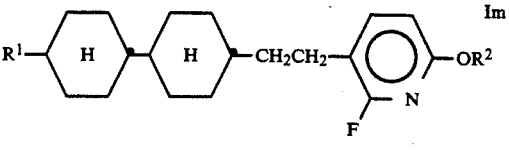
Im

-continued
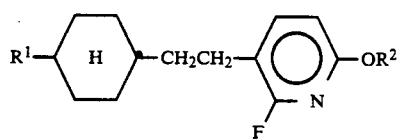   In
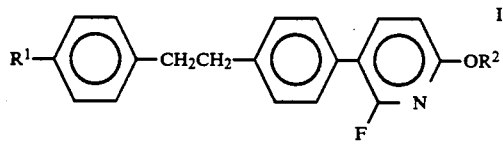   Io
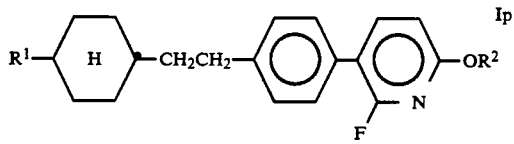   Ip
-continued
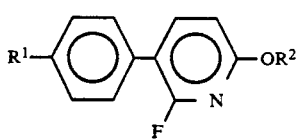   Iq
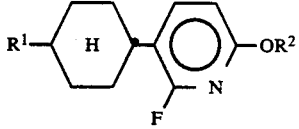   Ir
wherein
R¹ is a straight-chain alkyl, alkoxy, alkenyl, or oxaalykyl group with up to 15 C atoms in the alkyl residue, and
R² is alkyl, alkenyl, oxaalykyl, or alkylcarbonyl with up to 15 C atoms in the alkyl residue.
2. A pyridine derivative as in claim 1, wherein R¹ and R² are each alkyl with 2–9 C atoms.
* * * * *